(12) United States Patent
Shikaumi

(10) Patent No.: US 9,022,568 B2
(45) Date of Patent: May 5, 2015

(54) OPHTHALMOLOGIC IMAGING APPARATUS, METHOD OF CONTROLLING THE SAME, AND PROGRAM

(71) Applicant: Canon Kabushiki Kaisha, Tokyo (JP)

(72) Inventor: Masao Shikaumi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/246,445

(22) Filed: Apr. 7, 2014

(65) Prior Publication Data

US 2014/0313478 A1  Oct. 23, 2014

(30) Foreign Application Priority Data

Apr. 17, 2013  (JP) .................. 2013-086793

(51) Int. Cl.
*A61B 3/14* (2006.01)
*A61B 3/00* (2006.01)
*A61B 3/12* (2006.01)

(52) U.S. Cl.
CPC ........................ *A61B 3/12* (2013.01)

(58) Field of Classification Search
USPC ................................ 351/206, 246
See application file for complete search history.

(56) References Cited

U.S. PATENT DOCUMENTS

| 8,449,113 B2 | 5/2013 | Shikaumi |
| 8,449,114 B2 | 5/2013 | Ohban |
| 8,657,441 B2 | 2/2014 | Ohban |
| 2012/0050515 A1 | 3/2012 | Shikaumi et al. |
| 2012/0050677 A1 | 3/2012 | Ohban |
| 2013/0235345 A1 | 9/2013 | Ohban |

FOREIGN PATENT DOCUMENTS

| JP | 04-317628 A | 11/1992 |
| JP | 4430378 B2 | 3/2010 |
| JP | 2012-050592 A | 3/2012 |

*Primary Examiner* — Jack Dinh
(74) *Attorney, Agent, or Firm* — Fitzpatrick, Cella, Harper & Scinto

(57) ABSTRACT

There is provided an inexpensive ophthalmologic imaging apparatus having favorable operability in anterior ocular segment imaging and fundus imaging. In an ophthalmologic imaging apparatus which includes a focus lens located in an optical system, a focus lens drive unit configured to drive the focus lens, and a focusing operation unit configured to designate the drive amount of the focus lens, and has a fundus imaging mode of imaging a fundus and an anterior ocular segment imaging mode of imaging an anterior ocular segment, the drive amount of the focus lens by the focus lens drive unit is changed in accordance with a selected imaging mode and a focusing operation amount in the focusing operation unit.

11 Claims, 10 Drawing Sheets

OPHTHALMOLOGIC IMAGING APPARATUS, METHOD OF CONTROLLING THE SAME, AND PROGRAM

BACKGROUND OF THE INVENTION

1. Field of the Invention

The present invention relates to an ophthalmologic imaging apparatus and, more particularly, to an ophthalmologic imaging apparatus which can image the anterior ocular segment of an eye to be inspected, a method of controlling the same, and a program.

2. Description of the Related Art

Conventionally there has been known a fundus camera which allows an operator to observe and image the fundus and anterior ocular segment of an eye to be inspected. The fundus camera disclosed in Japanese Patent Application Laid-Open No. H04-317628 is configured to cope with imaging of the anterior ocular segment by separating the eye to be inspected from the fundus camera and moving the focus lens, which focuses an imaging plane relative to the eye to be inspected, in the hypermetropic direction.

In addition, the fundus camera disclosed in Japanese Patent Application Laid-open No. 2012-50592 is configured to insert a diopter correction lens and automatically move a focus lens to a predetermined position at the time of anterior ocular segment imaging to facilitate a switchover operation to anterior ocular segment imaging.

The fundus camera disclosed in Japanese Patent Application Laid-Open No. 2012-50592 facilitates operations for most operators. However, when performing anterior ocular segment imaging, different operators may have different regions of main interest, for example, an iris region and an eyelid region. In order to cover all these needs, it is necessary to set a wide focus adjustable range.

Japanese Patent No. 4430378 discloses the following technique to cope with the wide focus adjustment range for anterior ocular segment imaging in a fundus camera. This technique includes a barrel cam mechanism which converts the rotation of a barrel into linear movement along the optical axis of a focus lens, changes the tilt of the barrel cam between a focus area corresponding to fundus imaging and a focus area corresponding to anterior ocular segment imaging, and increases the tilt of the barrel cam corresponding to the unit rotational angle of the barrel in a focus area corresponding to anterior ocular segment imaging.

According to the technique disclosed in Japanese Patent No. 4430378, however, the use of different focus areas for anterior ocular segment imaging and fundus imaging makes it necessary to ensure a large drive area for the focus lens, resulting in an increase in apparatus size.

In addition, this technique requires the barrel cam, resulting in high cost.

Furthermore, this technique lacks flexibility in terms of focus lens drive amount corresponding to the unit rotational angle of the barrel at the time of anterior ocular segment imaging and at the time of fundus imaging, and hence has the problem of a low degree of freedom in operability setting when performing manual focusing.

SUMMARY OF THE INVENTION

The present invention provides an inexpensive ophthalmologic imaging apparatus having favorable manual focusing operability for anterior ocular segment imaging and fundus imaging.

In order to solve the above problems, there is provided an ophthalmologic imaging apparatus according to the present invention including an image pickup unit configured to capture an image of an eye to be inspected by receiving reflected light from the eye through an optical system, a focus lens located in the optical system, a focus lens drive unit configured to drive the focus lens, a focusing operation unit configured to designate a drive amount of the focus lens, and an imaging mode selection unit configured to select an imaging mode from a fundus imaging mode of imaging a fundus when imaging an eye to be inspected and an anterior ocular segment imaging mode of imaging an anterior ocular segment, the apparatus comprising a focus control unit configured to change a drive amount of the focus lens by the focus lens drive unit with respect to a focusing operation amount in the focusing operation unit in accordance with an imaging mode selected by the imaging mode selection unit.

The present invention can provide an inexpensive ophthalmologic imaging apparatus having favorable manual focusing operability for anterior ocular segment imaging and fundus imaging.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

First Embodiment

Figure 1:
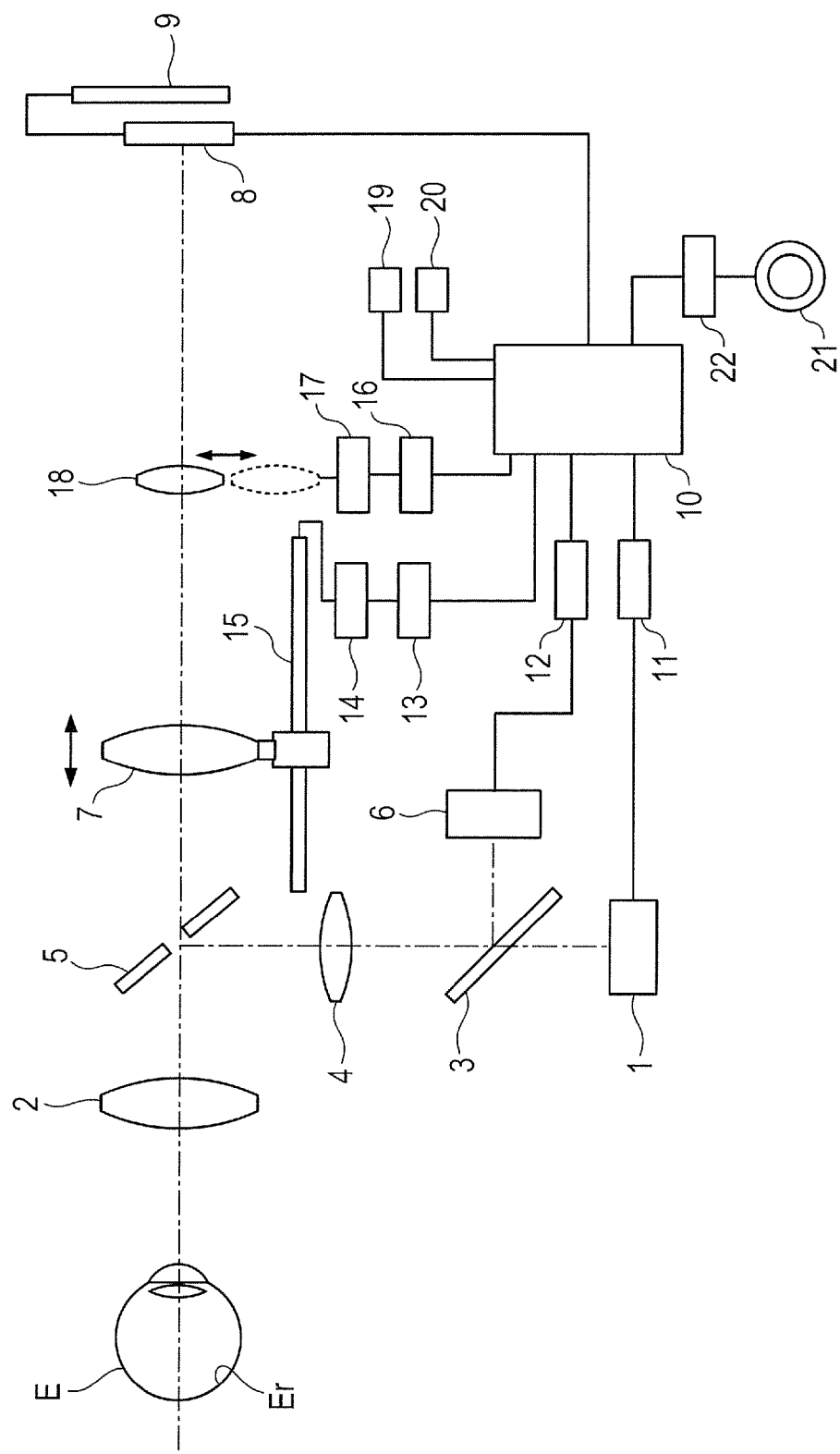
FIG. 1 is a view showing the arrangement of an ophthalmologic imaging apparatus according to the first embodiment.

FIG. 1 is a view showing the arrangement of a fundus camera according to the first embodiment which is used as an ophthalmologic imaging apparatus. The fundus camera of this embodiment is a non-mydriatic fundus camera. The fundus camera located in front of an eye E to be inspected incorporates an observation illumination optical system ranging from an observation light source 1, which is formed from, for example f an infrared LED and emits infrared light, to an objective lens 2 located in correspondence with the eye E. In this observation illumination optical system, the observation light source 1, a dichroic mirror 3, a relay lens 4, and a perforated mirror 5 are sequentially arranged. An imaging light source 6 formed from a xenon tube is located as an imaging illumination optical system in the incident direction of the dichroic mirror 3.

A focus lens 7 which adjusts focus by moving in the optical axis direction is located as an imaging optical system behind the perforated mirror 5. The fundus camera has an image pickup unit 8 arranged on an extension of the optical axis of the focus lens 7. The image pickup unit 8 is an image sensor such as a CCD or CMOS sensor, which can receive an image of an eye to be inspected, has sensitivity from a visible region to an invisible (near infrared) region, and can output moving images and still images.

An observation imaging optical system is formed from an optical system ranging from the objective lens 2 to the image pickup unit 8. The image pickup unit 8 according to the present invention corresponds to an image pickup unit which receives the light reflected by the eye E via the observation optical system and captures an image of the eye E. The focus lens 7 is located in the optical system as described above.

In addition, the fundus camera includes a monitor 9 which displays moving images or still images from the image pickup unit 8 and a control unit 10 which controls the overall system. The image pickup unit 8 described above is connected to the control unit 10.

Outputs of the control unit 10 are respectively connected to the observation light source 1 and the imaging light source 6 via drive circuits 11 and 12. The control unit 10 is also connected to a release switch 19. The control unit 10 is formed from a one-chip microcomputer or she like.

The control unit 10 is connected to an actuator 14 for driving the focus lens via a drive circuit 13. The actuator 14 is formed from a stepping motor as a known electric motor, and rotates by an amount proportional to the number of drive pulses as command values supplied from the control unit 10. The actuator 14 rotates a connected ball screw 15 in accordance with the rotation of the shaft, and linearly drives the focus lens 7 fixed to a nut on the ball screw 15 in the optical axis direction in accordance with the rotation. The arrangement configured to move the focus lens 7 along the optical axis of reflected light corresponds to a focus lens drive unit in the present invention.

The control unit 10 is connected to an actuator 17 via a drive circuit 16. The actuator 17 is driven to insert/retreat a diopter correction lens 18 into/from, an imaging optical path. The diopter correction lens 18 serves as a fundus imaging optical system while being outside the optical path and can capture an image of a fundus Er of the eye E.

The diopter correction lens 18 serves as a lens for anterior ocular segment imaging while being inside the imaging optical path, and can perform anterior ocular segment imaging for the iris, sclera (white of the eye), eyelid region, or the like of the eye E. The diopter correction lens 18 will be exemplified as a form of a diopter correction unit which corrects the diopter of the eye E in the present invention.

The fundus camera capable of diopter correction generally has two types of diopter correction lenses for excessive myopia and excessive hyperopia, and inserts one of them which is required for fundus imaging into the optical path.

When performing anterior ocular segment imaging, the camera inserts the diopter correction lens for excessive hyperopia into the optical path. For the sake of descriptive simplicity, FIG. 1 shows only the diopter correction lens for excessive hyperopia as the diopter correction lens 18.

The release switch 19 is connected to the control unit 10. A changeover switch 20 between anterior ocular segment imaging and fundus imaging is connected to the control unit 10.

When the operator presses the release switch 19, the control unit 10 transmits a release signal to the image pickup unit 8. This makes the image pickup unit 8 perform an imaging operation for a still image.

A focus dial 21 serves as an operation member for performing focus adjustment by a manual rotating operation. When the operator manually operates this dial, an operation amount detection unit 22 detects a rotating direction and a rotation amount by using a known two-phase pulse encoder, and inputs the resultant data to the control unit 10. The focus dial 21 will be exemplified as a form of a focusing operation unit which designates the drive amount of the focus lens 7 in the present invention.

Figure 2:
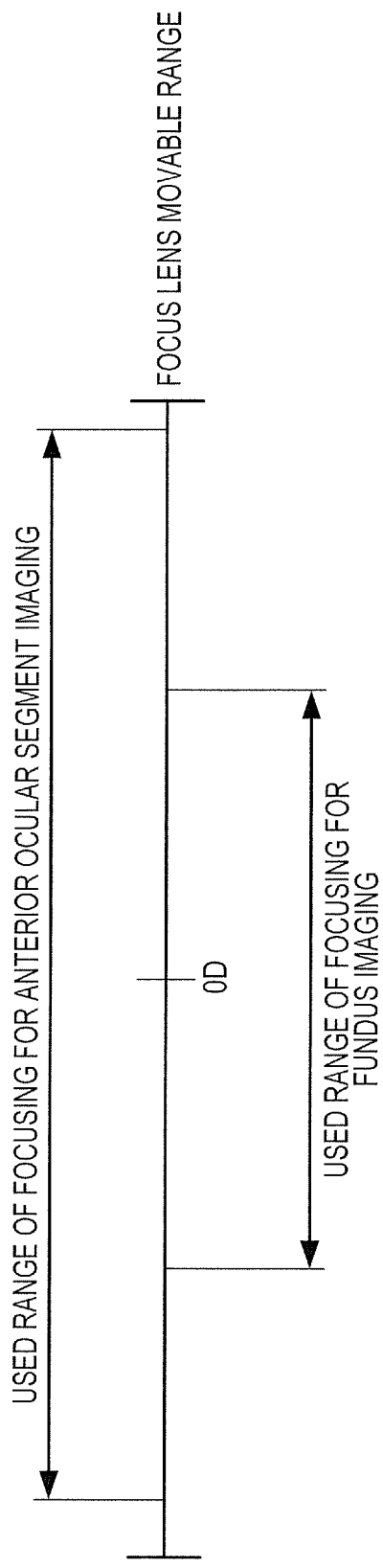
FIG. 2 is a view schematically showing a focus area in the first embodiment.

FIG. 2 is a view for schematically explaining the relationship between a mechanical movable range in the imaging optical axis direction of the focus lens 7, a used range of focusing for fundus imaging, and a used range of focusing for anterior ocular segment imaging.

The focus lens has focus ranges corresponding to predetermined diopters of an eye to be inspected in the myopia direction and the hyperopia direction with reference to a diopter of 0 D of the eye to be inspected at the time of fundus imaging.

In anterior ocular segment imaging, since the diopter correction lens 18 is inserted into the optical path, a reference to 0 D is not set. The region of main interest of the operator varies, including the iris portion and the eyelid portion, and in addition, the user has various requirements about field angles, for example, specific desired imaging ranges in the anterior ocular segment. In order to meet many requirements, as shown in FIG. 2, it is necessary to broaden the used range of focusing for anterior ocular segment imaging as compared with the used range of focusing for fundus imaging.

If the moving amount of the focus lens 7 in the optical axis direction (to be referred to as sensitivity for operation, hereinafter) relative to the operation amount of the focus dial 21 remains the same in anterior ocular segment imaging and fundus imaging, the operator operates the focus dial 21 more at the time of anterior ocular segment imaging, resulting in poor operability.

Figure 3:
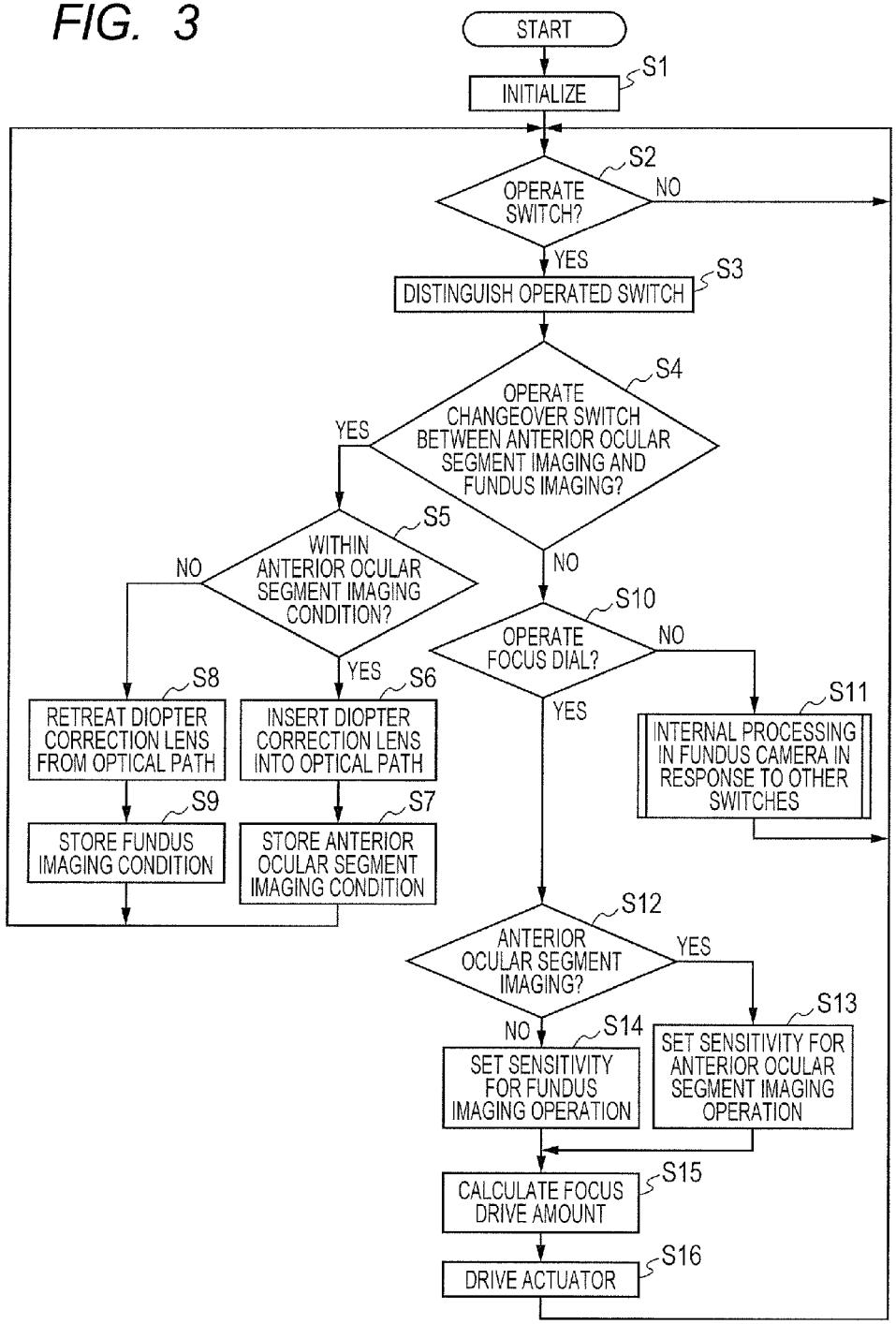
FIG. 3 is an operation flowchart of the ophthalmologic imaging apparatus according to the first embodiment.

FIG. 3 is a flowchart for explaining the operation of the fundus camera according to the first embodiment. In practice, this operation is implemented as a program for a one-chip microcomputer forming the control unit 10. The fundus camera described as an embodiment of the ophthalmologic imaging apparatus according to the present invention has a fundus imaging mode for imaging the fundus of an eye to be inspected, and an anterior ocular segment imaging mode for imaging the anterior ocular segment of an eye to be inspected.

First of all, when the operator turns on the power supply to start an operation, for example, the camera initializes the internal condition of the control unit 10 in step S1 in FIG. 3.

The process then advances to step S2 to wait for a switch operation on the fundus camera. The process repeats step S2 until the operator performs a switch operation. When the operator performs a switch operation, the process advances to step S3 to distinguish the operated switch.

The process then advances to step S4 to determine whether the operated switch is the changeover switch 20 between anterior ocular segment imaging and fundus imaging. The changeover switch 20 and an arrangement for switching between the imaging modes in accordance with an operation on the switch function as an imaging mode selection unit in the present invention. It the operated switch is the changeover switch 20 between anterior ocular segment imaging and fundus imaging, the process advances to step S5. In step S5, the control unit 10 refers to the condition of the imaging optical system which is stored in the memory in the control unit 10 and currently designated by the changeover switch 20.

If the control unit 10 determines in step S5 that the camera is in the anterior ocular segment imaging condition, the process advances to step S6 to insert the diopter correction lens 18 into the imaging optical path via the drive circuit 16 and the actuator 17. The process then advances to step S7 to store information indicating that the camera is currently in the anterior ocular segment imaging condition in the memory in the control, unit 10. The process then returns to step S2.

If the control unit 10 determines in step S5 that the camera is not in the anterior ocular segment imaging condition (is in the fundus imaging condition), the process advances to step S8 to retreat the diopter correction lens 18 from the imaging optical path via the drive circuit 16 and the actuator 17. The process then advances to step S9 to store information indicating that the camera is currently in the fundus imaging condition in the memory in the control unit 10. The process then returns to step S2.

If the control unit 10 determines in step S4 that the operated switch is not the changeover switch 20 between anterior ocular segment imaging and fundus imaging, the process advances to step S10. If the operated switch is not the focus dial 21, the process advances to step S11, in which the control unit 10 performs necessary internal processing corresponding to the operated switch.

If the operated switch is the focus dial 21, the process advances to step S12 to refer to the condition of the imaging optical system which is stored in the memory in the control unit 10 and is currently designated by the changeover switch 20.

If the camera is in the anterior ocular segment imaging condition, the process advances to step S13 to set sensitivity a for anterior ocular segment imaging operation as sensitivity for operation corresponding to the drive amount of the focus lens 7 which corresponds to the unit operation angle of the focus dial. The process advances to step S15.

If the control unit 10 determines in step S12 that the camera is in the fundus imaging condition, the process advances to step S14 to set sensitivity b for fundus imaging operation as sensitivity for operation. The process then advances to step S15.

The sensitivity a for anterior ocular segment imaging operation is set to be larger than the sensitivity b for fundus imaging operation:

$$a > b \tag{1}$$

In step S15, the control unit 10 calculates the drive amount of the focus lens 7 by multiplying an operation amount p of the focus dial 21 by the sensitivity for operation. A drive amount is given as ap for anterior ocular segment imaging and as bp for fundus imaging.

The process then advances to step S16 to drive the focus lens 7 by driving the actuator 14 via the drive circuit 13 in accordance with the drive amount of the focus lens 7 calculated in step S15. The process then returns to step S2.

With the above operation, it is possible to almost equalize an operational feeling for focusing operation at the time of anterior ocular segment imaging relative to the operation angle of the focus dial 21 to that at the time of fundus imaging relative to the operation angle of the focus dial 21 by increasing the sensitivity for anterior ocular segment imaging as compared with that for fundus imaging, thus improving the operability. That is, the present invention is configured to improve operability by changing the drive amount of the focus lens by the focus lens drive unit, which corresponds to the focusing operation amount of the focusing operation unit, in accordance with the imaging mode selected by the imaging mode selection unit, by using a module area functioning as a focus control unit in the control unit 10. The above sensitivities a and b correspond to coefficients used for the decision of a focus lens drive amount by the focus lens drive unit in accordance with a focusing operation amount of the focusing operation unit in the present invention, and are stored in a module area functioning as a storage unit in the control unit 10. In addition, a module area functioning as a coefficient setting unit in the control unit 10 executes the decision of the coefficients to be used.

This embodiment has exemplified the case in which a stepping motor is used as the actuator 14 for driving the focus lens 7. It is also possible to use a DC motor or the like as an actuator. In this case, the embodiment uses a linear encoder or potentiometer for the detection of the position of the focus lens, and can set the sensitivity for operation by saving the value obtained by A/D-converting the number of pulses from the linear encoder or a voltage value indicating the position of the potentiometer and the operation amount of the focus dial 21.

In addition, it is obvious that a trackball, lever, or the like can be used in place of the dial as a focusing operation member.

Second Embodiment

The second embodiment of the present invention will be described next.

In anterior ocular segment imaging, operators differ in their regions of main interest, but a specific operator tends to perform imaging under predetermined conditions unique to him/her. In such a case, the operator does not always use the entire movable range of focusing for anterior ocular segment imaging, and hence allowing the operator to finely set a specific range of focusing will provide better usability.

The second embodiment has been made in consideration of this point and is configured to switch between at least two types of sensitivities for anterior ocular segment imaging operation, namely fine alignment and rough alignment.

Figure 4:
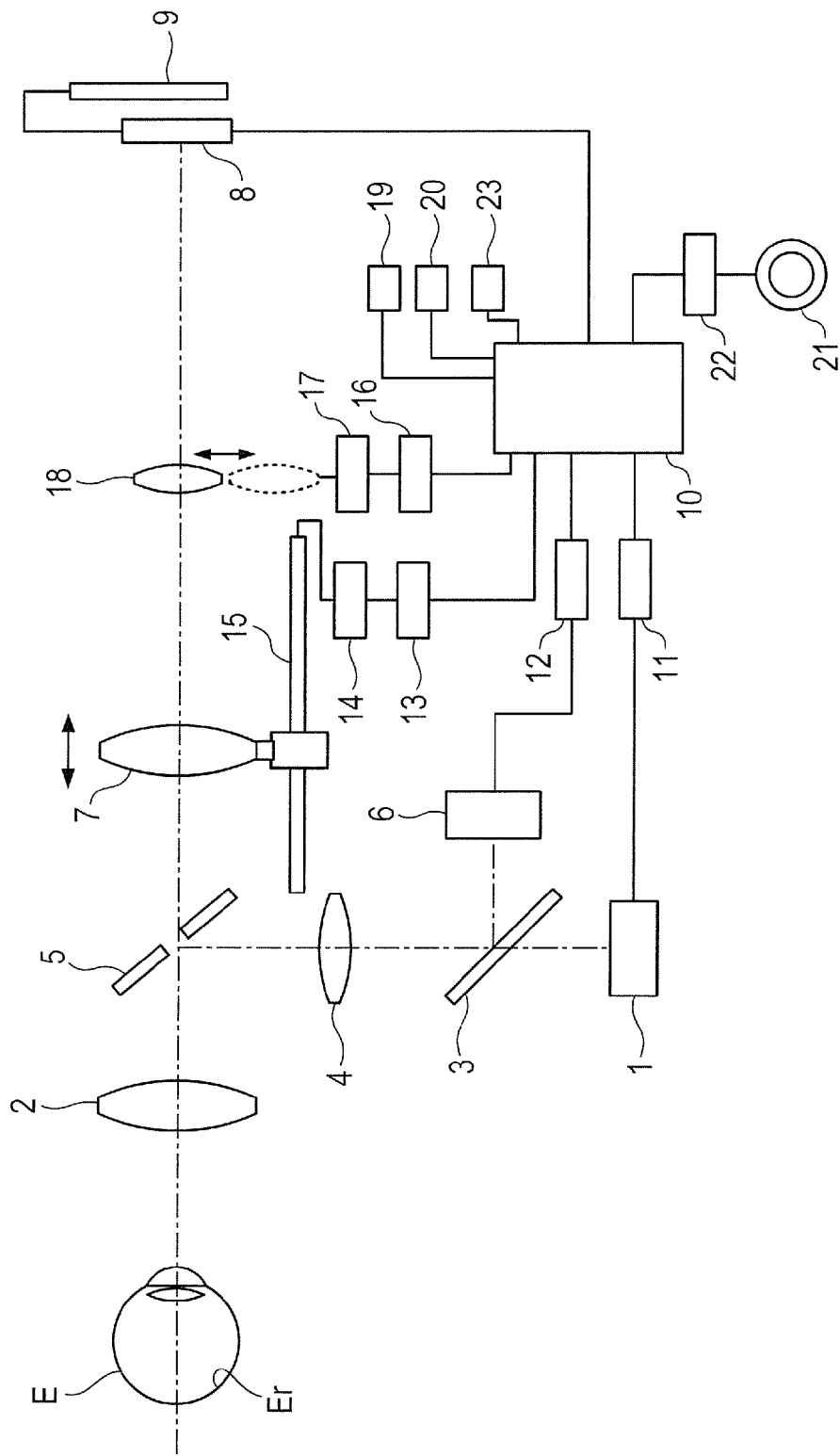
FIG. 4 is a view showing the arrangement of an ophthalmologic imaging apparatus according to the second embodiment.

The second embodiment will be described below with reference to FIG. 4. FIG. 4 is a view showing the arrangement of an ophthalmologic imaging apparatus according to the second embodiment. The same reference numerals as in FIG. 1 denote the same components in FIG. 4, and a description of them will be omitted.

This embodiment adds an anterior ocular segment operation amount, sensitivity changeover switch 23 to a control unit 10. It is possible to switch between two types of sensitivities of fine alignment and rough alignment for anterior ocular segment imaging operation sensitivity by operating the anterior ocular segment operation amount sensitivity changeover switch 23.

Figure 5:
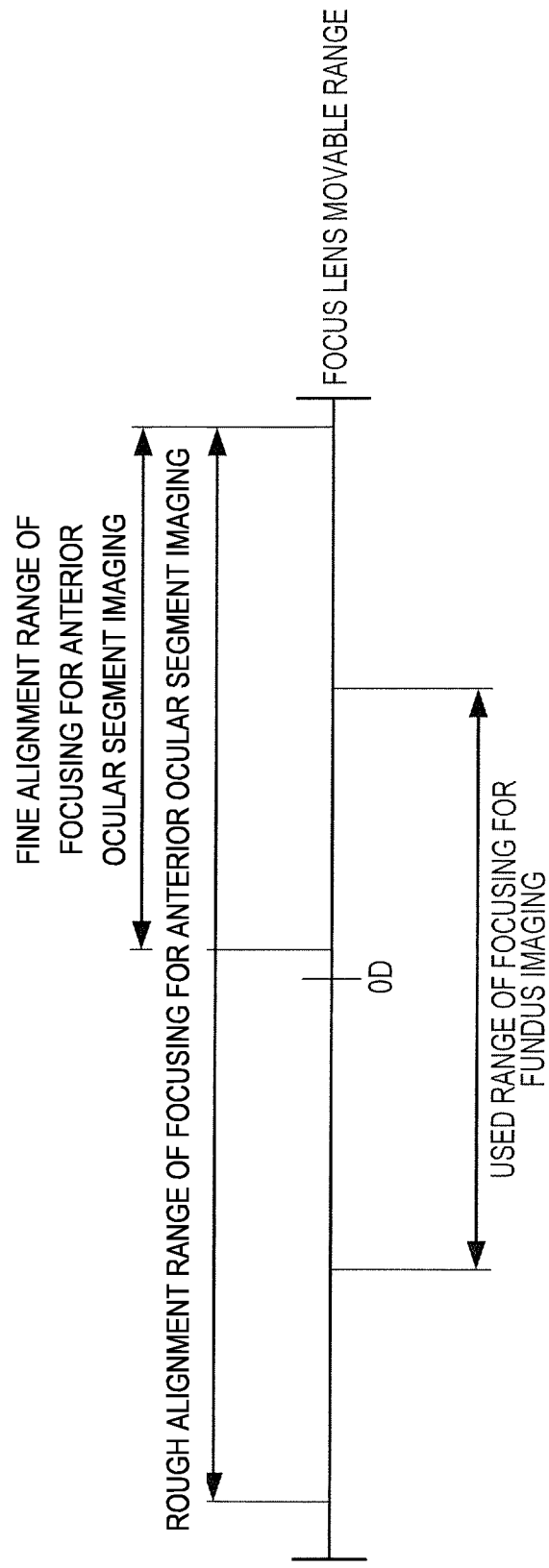
FIG. 5 is a view schematically showing a focus area in the second, embodiment.

FIG. 5 is a view for schematically explaining the relationship between a mechanical movable range in the imaging optical axis direction, of a focus lens 7, a used range of focusing for fundus imaging, and a used range of focusing for anterior ocular segment imaging according to the second embodiment.

FIG. 5 schematically shows the difference in size between a focus lens drive range when the sensitivity for anterior ocular segment imaging operation is set to rough alignment and when the sensitivity for anterior ocular segment imaging operation is set to fine alignment.

The operation of the second embodiment will be described next with reference to FIG. 6.

Figure 6:
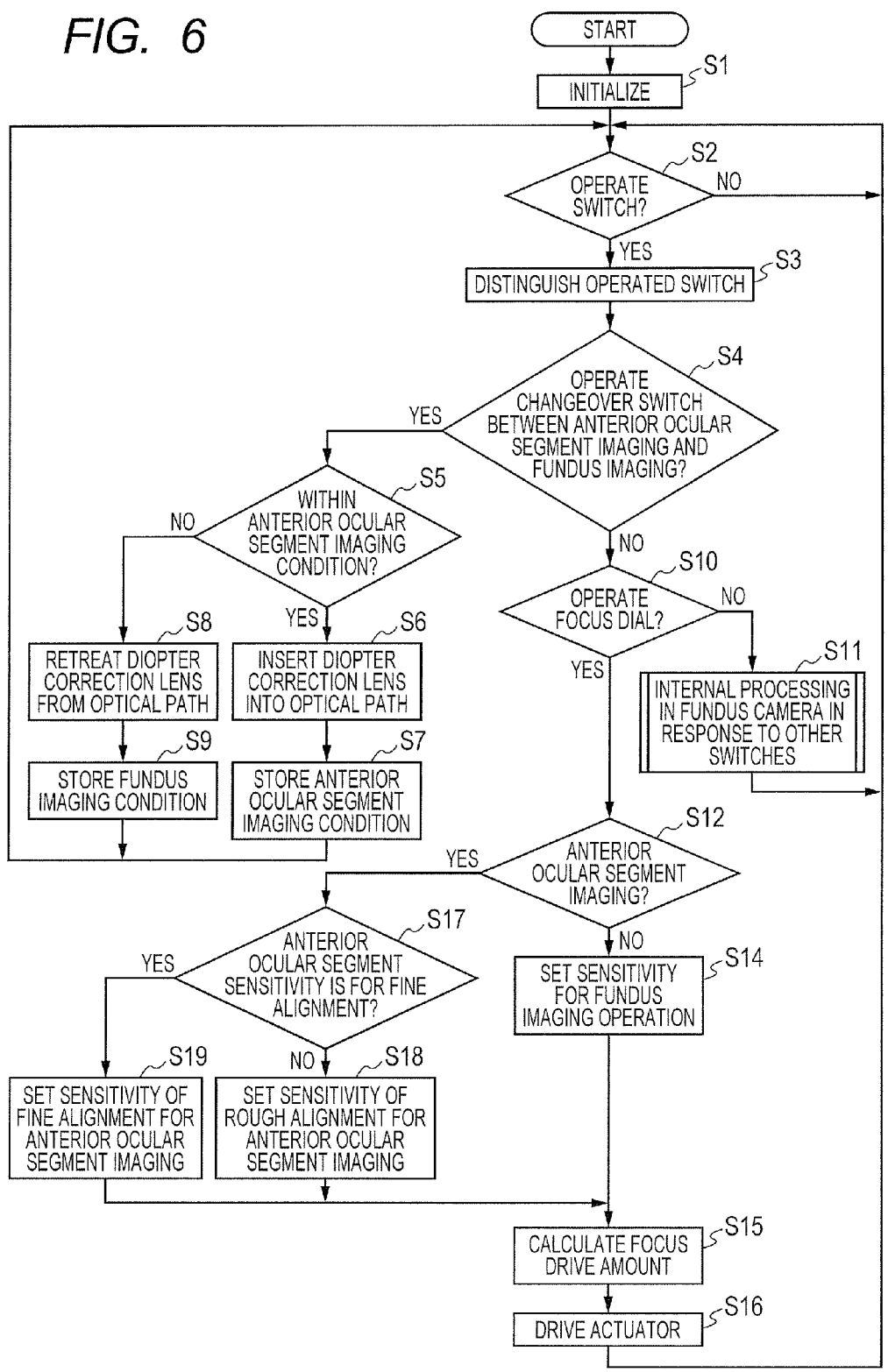
FIG. 6 is an operation flowchart of the ophthalmologic imaging apparatus according to the second embodiment.

FIG. 6 is a flowchart for explaining the operation of a fundus camera according to the second embodiment. The same step numbers as in FIG. 3 denote the steps indicating the same operations in FIG. 6, and a description of them will be omitted.

The difference from FIG. 3 is in processing in step S17 and the subsequent steps in which the process advances in the anterior segment imaging condition after the process advances from step S10 of detect the operation of a focus dial 21 to step S12 of determining whether the current condition is the anterior ocular segment imaging condition.

In step S17, the camera detects the condition of the anterior ocular segment operation amount sensitivity changeover switch 23. If the anterior ocular segment imaging operation amount sensitivity is set to rough alignment, the process advances to step S18 to set sensitivity of rough alignment as sensitivity for anterior ocular segment imaging operation. The process then advances to step S15.

In addition, if the anterior ocular segment imaging operation amount sensitivity is set to fine alignment, the process advances to step S19 to set sensitivity of fine alignment as sensitivity for anterior ocular segment imaging operation. The process then advances to step S15.

Using the anterior ocular segment operation amount sensitivity changeover switch 23 in this manner can switch between the two types of sensitivities for anterior ocular segment imaging operation, namely rough alignment and fine alignment.

The second embodiment has the effect of being able to meet needs of many operators by having a plurality of anterior ocular segment imaging operation amount sensitivities.

The embodiment described above has two types of operation sensitivities, namely rough alignment and fine alignment, as sensitivities for anterior ocular segment imaging operations. Obviously, however, three or more types of sensitivities for operations may be prepared, and the embodiment may switch between them by using the anterior ocular segment operation amount sensitivity changeover switch 23.

Third Embodiment

The third embodiment of the present decent roc will be described next.

As described in the second embodiment, a specific operator tends to perform anterior ocular segment imaging under predetermined conditions unique to him/her. For this reason, enabling the operator to set a range of focusing for anterior ocular segment imaging by himself/herself can further improve the operability. The third embodiment is configured to nave such an arrangement.

Figure 7:
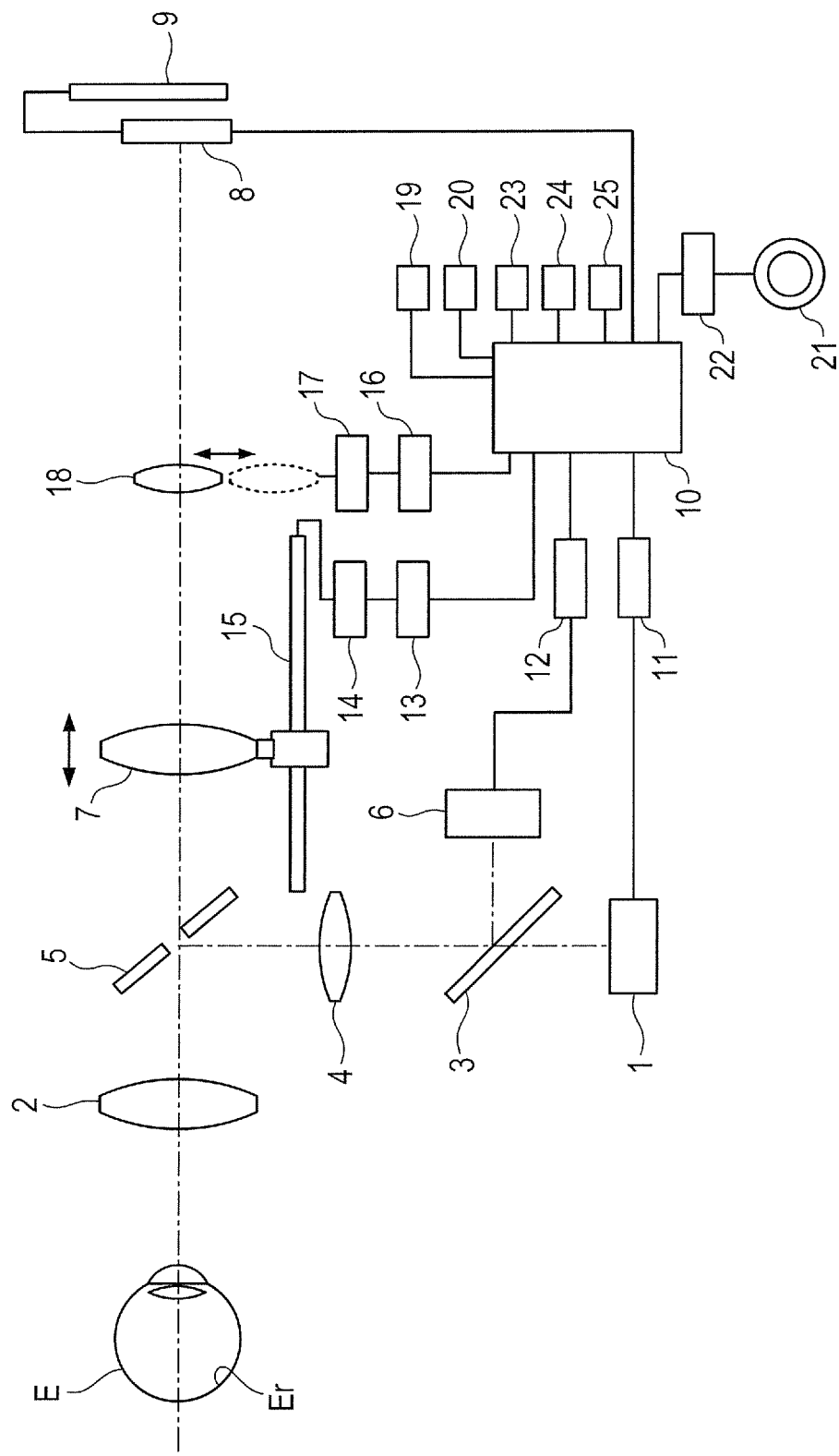
FIG. 7 is a view showing the arrangement of an ophthalmologic imaging apparatus according to the third embodiment.

The third embodiment will be described below with reference to FIG. 7. FIG. 7 is a view showing the arrangement of an ophthalmologic imaging apparatus according to the third embodiment. The same reference numerals as in FIGS. 1 and 4 denote the same components in FIG. 7, and a description of them will be omitted.

This embodiment adds a focusing position set switch 24 for anterior ocular segment and a focusing position return switch 25 for anterior ocular segment to a control unit 10.

When the operator operates the focusing position set switch 24 for anterior ocular segment in an anterior ocular segment imaging condition, the control unit 10 stores the anterior ocular segment focusing position at the time of the operation.

In addition, assume that the operator operates the focusing position return switch 25 for anterior ocular segment in an anterior ocular segment imaging condition. In this case, when a focusing position for anterior ocular segment is stored, the control unit 10 calls a stored focusing position, for anterior ocular segment and moves a focus lens 7 to the stored focusing position for anterior ocular segment. A module area functioning as a focusing position storage unit in the control unit 10 stores a focusing position as a position on the optical axis at which this focus lens is stopped. In addition, the control unit 10 calls the focusing position from the focusing position storage unit. A module area functioning as a focusing position return unit returns the focus lens to the called focusing position.

In addition, in this case, the control unit 10 sets sensitivity for manual focusing operation to fine alignment to facilitate fine manual focus adjustment before and after the called, focusing position for anterior ocular segment.

Figure 8:
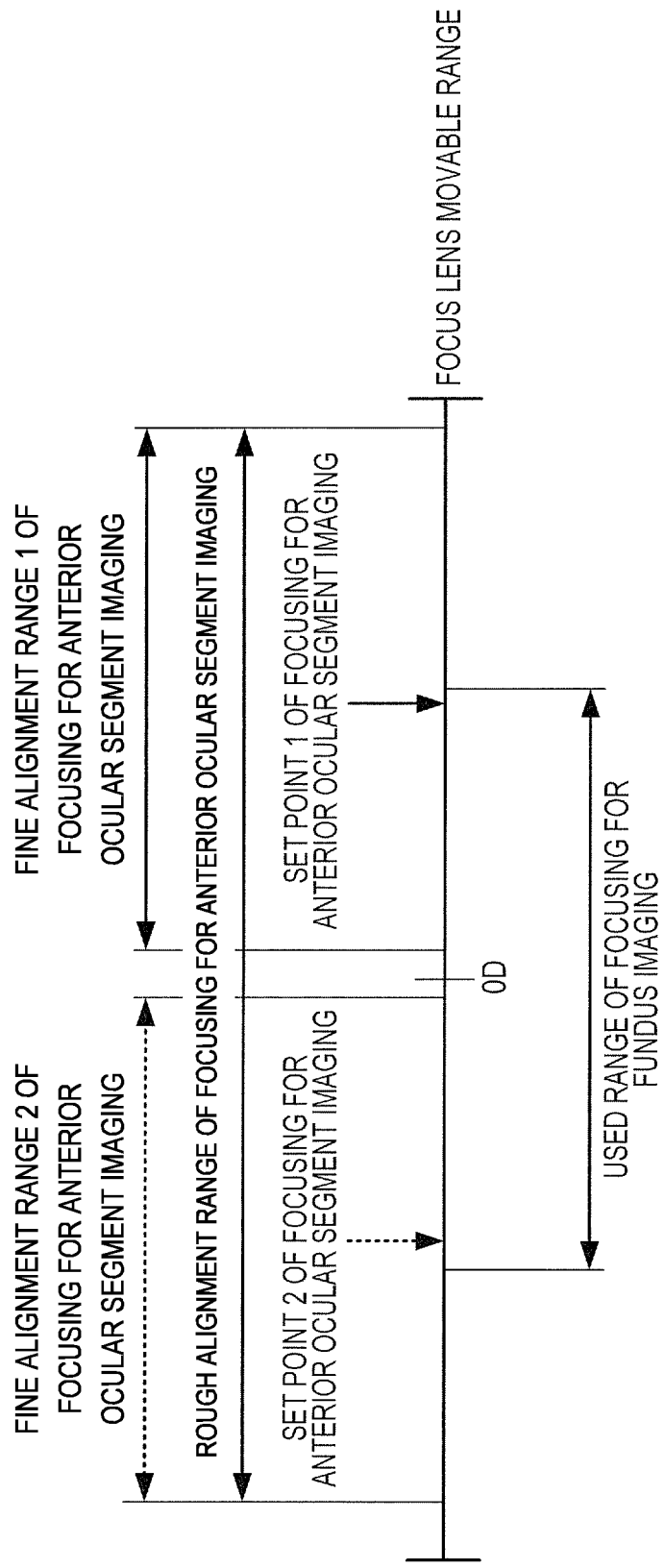
FIG. 8 is a view schematically showing a focus area in the third embodiment.

FIG. 8 is a view for schematically explaining the relationship between a mechanical movable range in the imaging optical axis direction of the focus lens 7, a used range of focusing for fundus imaging, and a used range of focusing for anterior ocular segment imaging according to the third embodiment.

FIG. 8 shows that when a focusing position for anterior ocular segment has been set, the camera sets sensitivity of fine alignment in accordance with the position, and changes the focus lens drive range.

The operation of the third embodiment will be described next with reference to FIG. 9.

Figures 9, 9A:
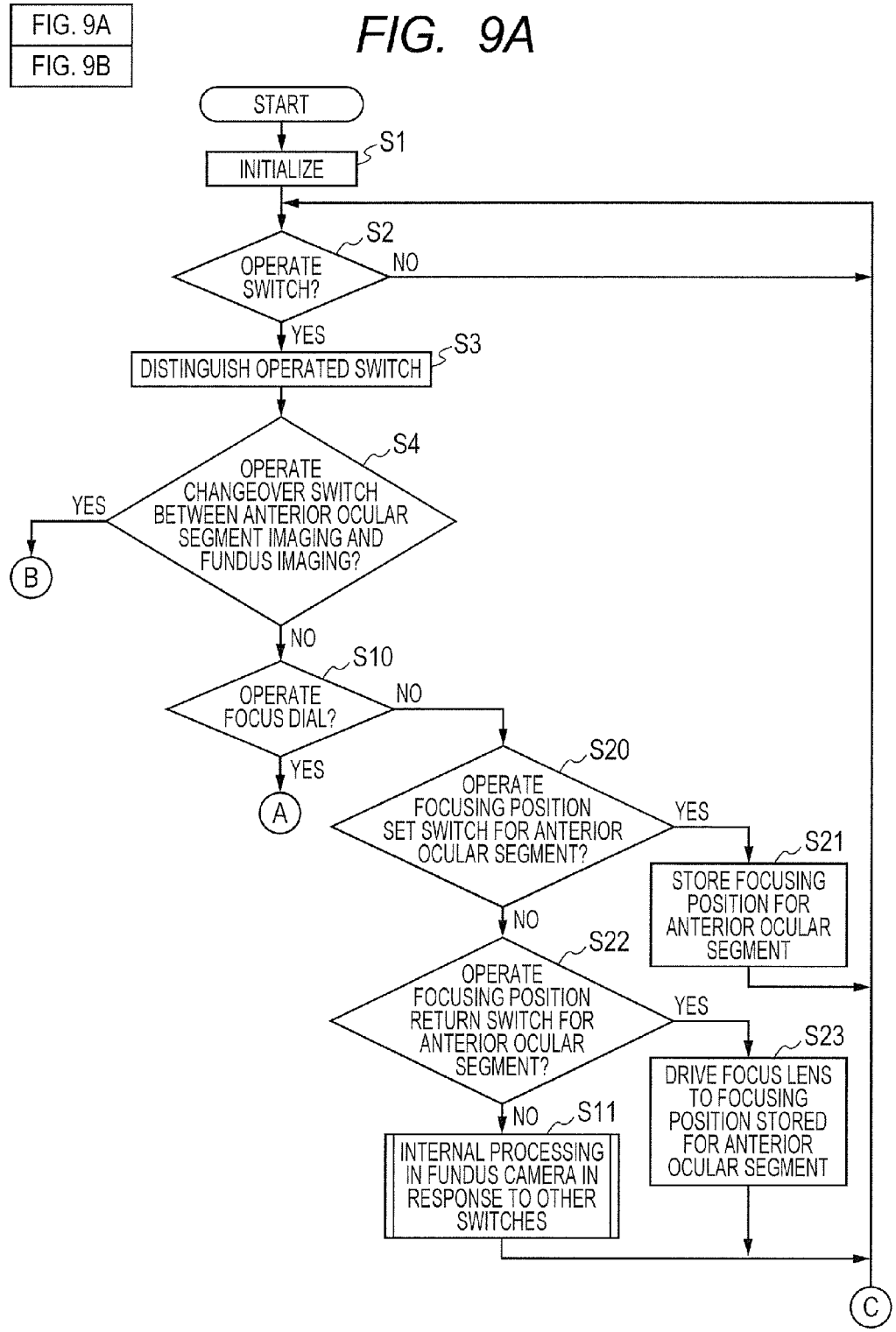
FIG. 9 is comprised of FIGS. 9A and 9B showing an operation flowchart of the ophthalmologic imaging apparatus according to the third embodiment.
Figure 9B:
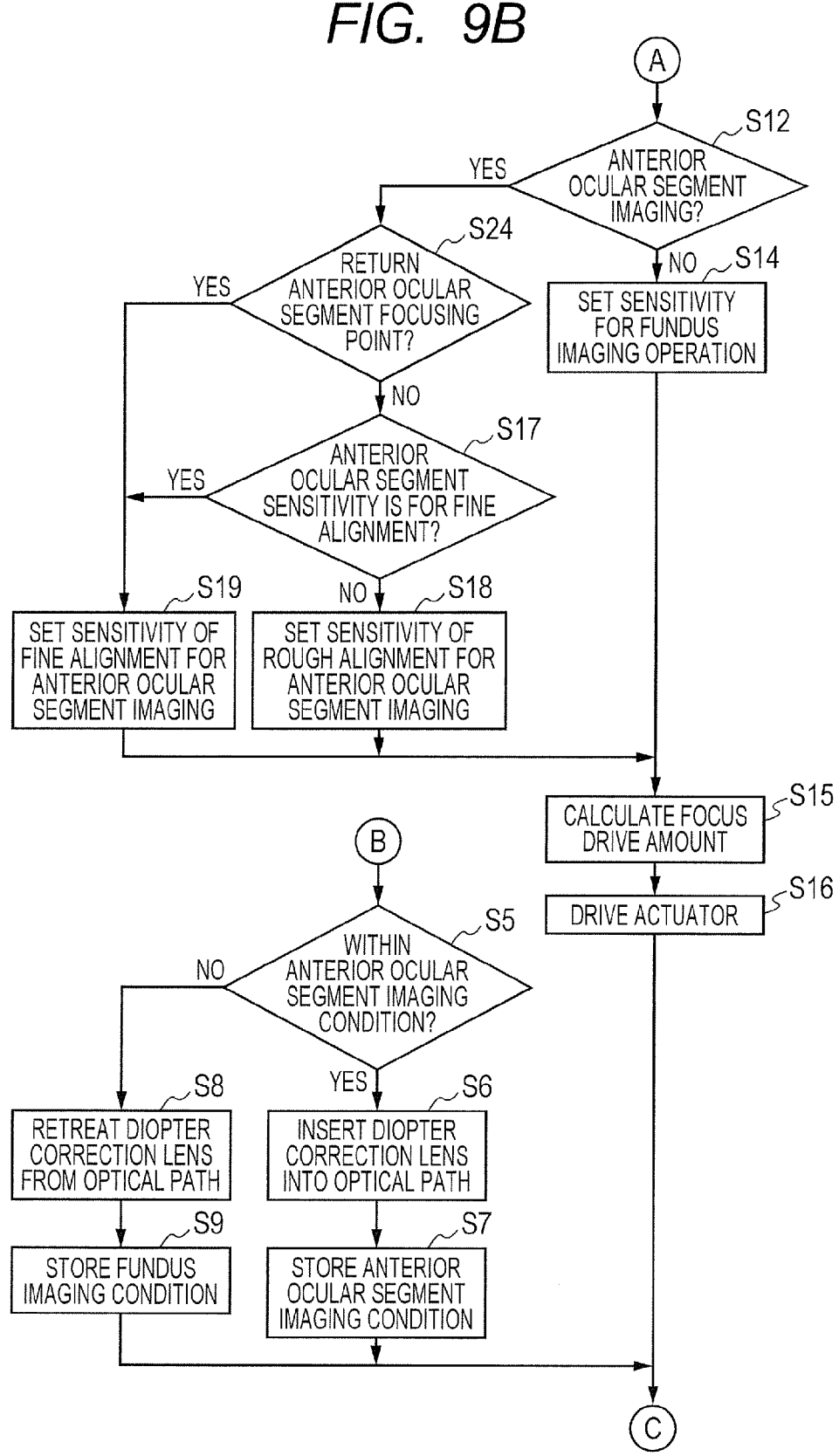

FIG. 9 is a flowchart for explaining the operation of the fundus camera according to the third embodiment. The same step numbers as in FIGS. 3 and 6 denote the steps indicating the same operations in FIG. 9, and a description of them will be omitted.

If the camera determines in step S10 that the operated switch is not the focus dial 21, the process advances to step S20.

In step S20, the camera determines whether the operated switch is the focusing position set switch 24 for anterior ocular segment. If the operated switch is the focusing position set switch 24 for anterior ocular segment, the process advances to step S21 to store the current position of the focus lens 7 as a focusing position for anterior ocular segment in the memory in the control unit 10. The process then returns to step S2.

If the camera determines in step S20 that the operated switch is not the focusing position set switch 24 for anterior ocular segment, the process advances to step S22.

In step S22, the camera determines whether the operated switch is the focusing position return switch 25 for anterior ocular segment. If the operated switch is the focusing position return switch 25 for anterior ocular segment, the process advances to step S23 to call the set focusing position for anterior ocular segment from the memory in the control unit 10, and moves the focus lens 7 to the focusing position for anterior ocular segment via the drive circuit 13 and the actuator 14. The process then returns to step S2.

If the camera determines in step S22 that the operated switch is not the focusing position return switch 25 for anterior ocular segment, the process advances to step S11 to perform processing corresponding to the operated switch. The process then returns to step S2.

If the camera determines in step S12 that it is currently set in an anterior ocular segment imaging condition, the process advances to step S24. In step S24, the camera determines whether a focusing position for anterior ocular segment is set.

If NO in step S24, the process advances to step S17 to perform the same operation as that described in the second embodiment. If a focusing position for anterior ocular segment is set, the process advances to step S19 to automatically set the sensitivity for operation to sensitivity of fine alignment for focusing position fine alignment.

As described above, the third embodiment enables the operator to set a focusing position for anterior ocular segment and call the position, and improves operability by automatically setting the sensitivity for operation to sensitivity of fine alignment when the operator calls the set focusing position.

In addition, if no focusing position for anterior ocular segment is set, the embodiment sets the sensitivity for operation to sensitivity of rough alignment to cope with a wide range of focusing for anterior ocular segment imaging.

As has been described above, the present invention can improve operability in manual focusing operations for anterior ocular segment imaging and for fundus imaging.

Note that the present invention is not limited to the contents described in the embodiments, and various modifications and the like can be made within the scope of the appended claims.

Other Embodiments

The present invention is also implemented by executing the following processing. That is, this is the processing of supplying software (programs) for implementing the functions of the above embodiments to a system or apparatus via a network or various types of storage media and making the computer (or the CPU, MPU, or the like) of the system or apparatus read out and execute the software.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-086793, filed Apr. 17, 2013, which is hereby incorporated by reference herein in its entirety.

What is claimed is:

1. An ophthalmologic imaging apparatus comprising:
an image pickup unit configured to capture an image of an eye to be inspected by receiving reflected light from the eye through an optical system;
a focus lens located in the optical system;
a focus lens drive unit configured to drive the focus lens;
a focusing operation unit configured to designate a drive amount of the focus lens;
an imaging mode selection unit configured to select an imaging mode from a fundus imaging mode of imaging a fundus when imaging an eye to be inspected and an anterior ocular segment imaging mode of imaging an anterior ocular segment; and
a focus control unit configured to change a drive amount of the focus lens by the focus lens drive unit with respect to a focusing operation amount in the focusing operation unit in accordance with an imaging mode selected by the imaging mode selection unit.

2. An apparatus according to claim 1, wherein the focus lens drive unit linearly drives the focus lens in an optical axis direction by using an electric motor and a ball screw.

3. An apparatus according to claim 1, further comprising:
a storage unit configured to have a plurality of coefficients used to decide a drive amount of the focus lens by the focus lens drive unit in accordance with the focusing operation amount in the focusing operation unit in the anterior ocular segment imaging mode; and
a coefficient setting unit configured to decide the coefficient to be used.

4. An apparatus according to claim 3, further comprising:
a focus position storage unit configured to store a focusing position at which the focus lens is stopped in the anterior ocular segment imaging mode; and
a focusing position return unit configured to call the focusing position stored in the focusing position storage unit and return the focus lens to the focusing position,
wherein the coefficient setting unit decides the coefficient as a coefficient for fine alignment for a focusing position, when a focusing position is stored in the focusing position storage unit.

5. An apparatus according to claim 1, further comprising:
a diopter correction unit configured to correct a diopter of the eye; and
a diopter correction switchover unit configured to switch between a case of using the diopter correction unit and a case of not using the diopter correction unit,
wherein the diopter correction switchover unit performs a switchover operation for the diopter correction unit in accordance with the imaging mode selected by the imaging mode selection unit.

6. A method of controlling an ophthalmologic imaging apparatus including (a) an image pickup unit configured to capture an image of an eye to be inspected by receiving reflected light from the eye through an optical system, (b) a focus lens located in the optical system, (c) a focus lens drive unit configured to drive the focus lens, (d) a focusing operation unit configured to designate a drive amount of the focus lens, and (e) an imaging mode selection unit configured to select an imaging mode from a fundus imaging mode of imaging a fundus when imaging an eye to be inspected and an anterior ocular segment imaging mode of imaging an anterior ocular segment, the method comprising steps of:
selecting the imaging mode by using the imaging mode selection unit;
changing a drive amount of the focus lens by using the focus lens drive unit with respect to a focusing operation amount in the focusing operation unit in accordance with the selected imaging mode; and
driving the focus lens by using the focus lens drive unit in accordance with the changed focus lens drive amount when causing the focusing operation unit to designate a drive amount of the focus lens.

7. A method according to claim 6, wherein the focus lens is linearly operated in an optical axis direction of the reflected light received by the image pickup apparatus.

8. A method according to claim 6, wherein a plurality of coefficients to be used to decide the focus lens drive amount by the focus lens drive unit in accordance with the focusing operation amount in the focusing operation unit are stored, and
wherein the coefficient is selected when the focus lens drive amount by the focus lens drive unit is changed in accordance with a focusing operation amount in the focusing operation unit.

9. A method according to claim 8, further comprising steps of:
storing a focusing position at which the focus lens is stopped in the anterior ocular segment imaging mode; and
calling the stored focusing position and returning the focus lens to the focusing position, wherein when the coefficient is selected, the coefficient is selected as a coefficient for fine alignment for a focusing position, if the focusing position is stored.

10. A method according to claim 6, further comprising a step of inserting a diopter correction unit configured to correct a diopter of the eye to be inspected, on an optical axis of the reflected light received by the imaging apparatus, when the anterior ocular segment imaging mode is selected.

11. A program for causing a computer to execute each step in a method defined in claim 6.

\* \* \* \* \*